United States Patent [19]
Chen

[11] Patent Number: 4,877,510
[45] Date of Patent: Oct. 31, 1989

[54] APPARATUS FOR PREPARATIVE GEL ELECTROPHORESIS

[75] Inventor: Jin-Hai Chen, Santa Monica, Calif.

[73] Assignee: Bio-Rad Laboratories, Inc., Hercules, Calif.

[21] Appl. No.: 262,905

[22] Filed: Oct. 25, 1988

[51] Int. Cl.$^4$ .................... G01N 27/28; G01N 27/26
[52] U.S. Cl. ............................ 204/299 R; 204/182.8
[58] Field of Search ................ 204/182.8, 299 R, 301

[56] References Cited

U.S. PATENT DOCUMENTS

| | | | |
|---|---|---|---|
| 3,346,479 | 10/1967 | Natelson | 204/301 |
| 3,375,187 | 3/1968 | Buchler | 204/301 |
| 3,539,493 | 11/1970 | Dorman | 204/299 |
| 3,616,454 | 10/1971 | Levy et al. | 304/299 |
| 3,640,813 | 2/1972 | Nerenberg | 204/299 |
| 3,697,406 | 10/1972 | Svendsen | 204/299 R |
| 3,773,648 | 11/1973 | Van Welzen et al. | 204/299 |
| 3,791,950 | 2/1974 | Allington | 204/182.8 X |
| 3,902,986 | 9/1975 | Nees | 204/299 |
| 3,980,546 | 9/1976 | Caccavo | 204/182.8 X |
| 4,111,785 | 9/1978 | Roskam | 204/299 R |
| 4,479,861 | 10/1984 | Hediger | 204/180 |
| 4,699,706 | 10/1987 | Burd et al. | 204/182.8 X |

FOREIGN PATENT DOCUMENTS

| | | | |
|---|---|---|---|
| 8021679 | 3/1973 | Japan | 204/182.8 |
| 434985 | 1/1975 | U.S.S.R. | 204/299 R |
| 616568 | 7/1978 | U.S.S.R. | 204/182.8 |

OTHER PUBLICATIONS

Camag, Inc. product literature.
Jovin et al., "An Apparatus for Preparative Temperature-Regulated Polyacrylamide Gel Electrophoresis," *Analytical Biochemistry*, 9, 351–369 (1964).
Koziarz et al., "A System for Preparative Polyacrylamide Gel Electrophoresis in Sodium Dodecyl Sulfate," *Analytical Biochemistry*, 86 78–89 (1978).
Giacobino et al., "The Use of Preparative SDS Polyacrylamide Gel Electrophoresis With Continuous Elution in the Purification of Membrane Proteins," *Receptor Purification Procedures*, 97–107.
Ryan et al., "Modification of the Shandon Southern Apparatus MK II for SDS Preparative Polyacrylamide Gel Electrophoresis," *Analytical Biochemistry*.
Hagen, "Large-Scale Preparative Polyacrylamide Gel Electrophoresis of Ribonucleic Acid," *Analytical Biochemistry*, 93, 299–305 (1979).
Shimada et al., "A New Device of Preparative Polyacrylamide Gel Electrophoresis and Its Application to Analysis of Cellular RNA," *Analytical Biochemistry*, 51, 456–465 (1973).
Malacinski, "Preparative Gel Electrophoresis of Ribonucleic Acids," Short Communications, 288–291 (1970).
BRL Product Literature.
Tara Scientific Ltd. product literature.
How the Poly-Prep Operates Product literature.
Savant Instruments, Inc. product literature.
Shandon product literature.

*Primary Examiner*—John F. Niebling
*Assistant Examiner*—John S. Starsiak, Jr.
*Attorney, Agent, or Firm*—Townsend and Townsend

[57] ABSTRACT

Emerging solutes from a preparative gel electrophoresis column are drawn into a narrow transfer tube through a collar which fits over the column end and secures a porous plate and dialysis membrane to the column end. The collar is provided with a series of channels running from the collar exterior to a series of locations on its interior wall based around the periphery of the porous plate. An external pump draws lower buffer solution into these channels and laterally through the porous plate to essentially located withdrawal tubing. The solutes emerging from the tubing are then directed to a fraction collector.

22 Claims, 4 Drawing Sheets

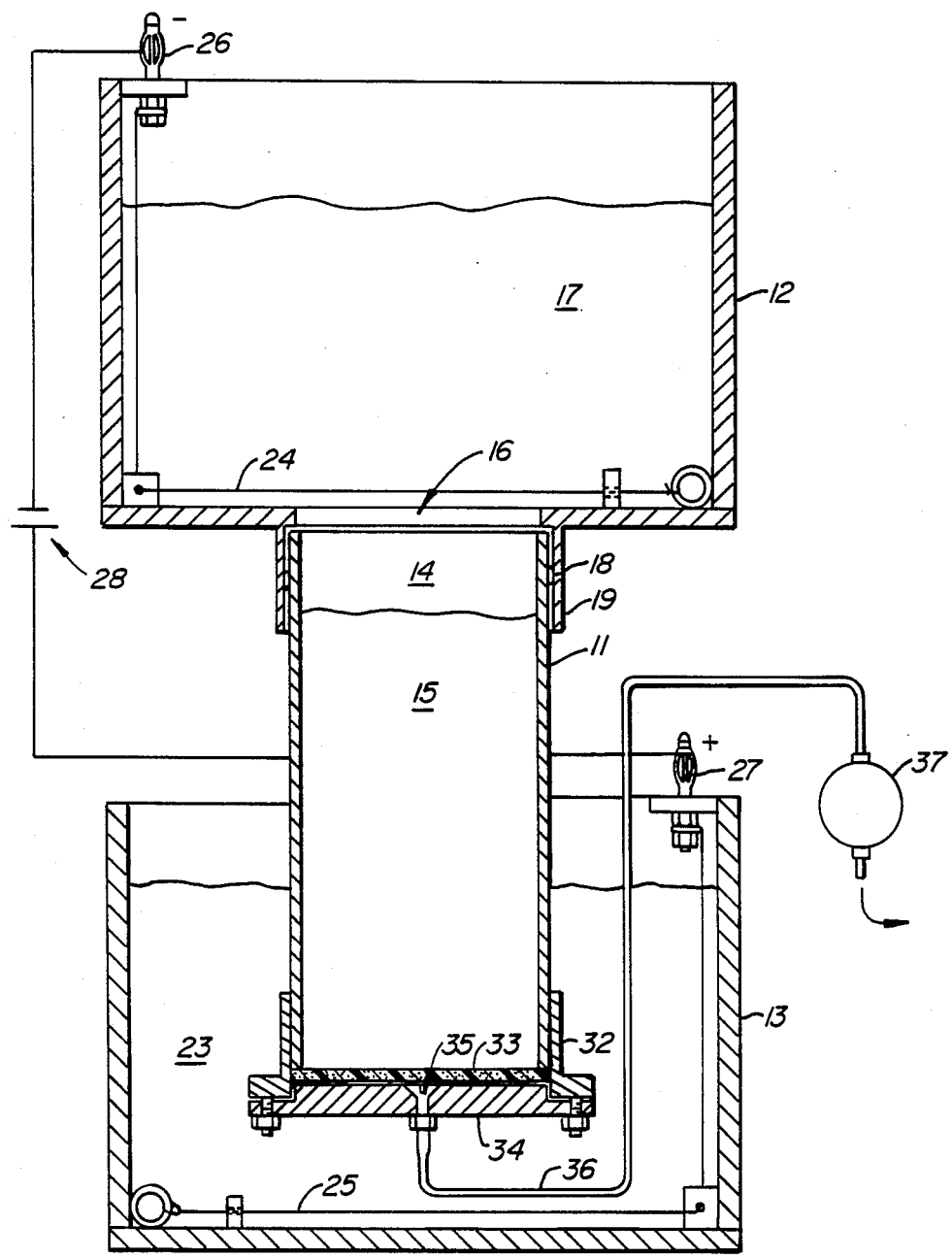
FIG._1.

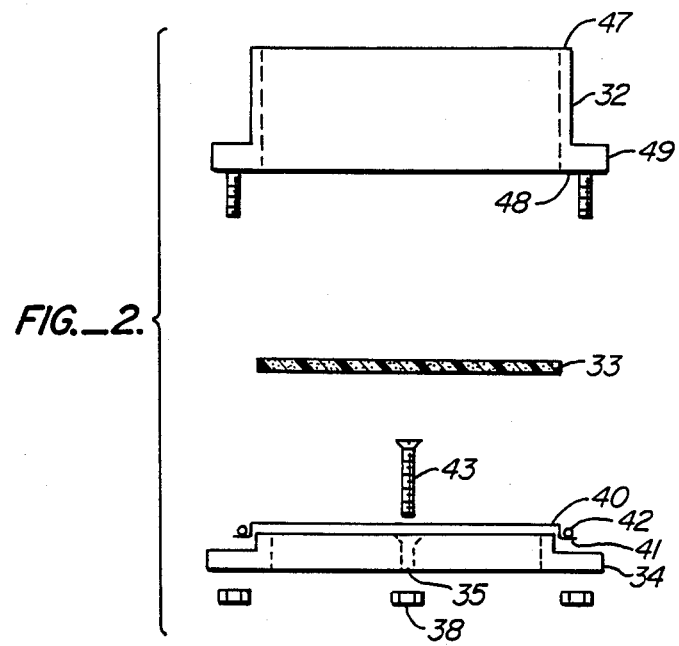
FIG._2.
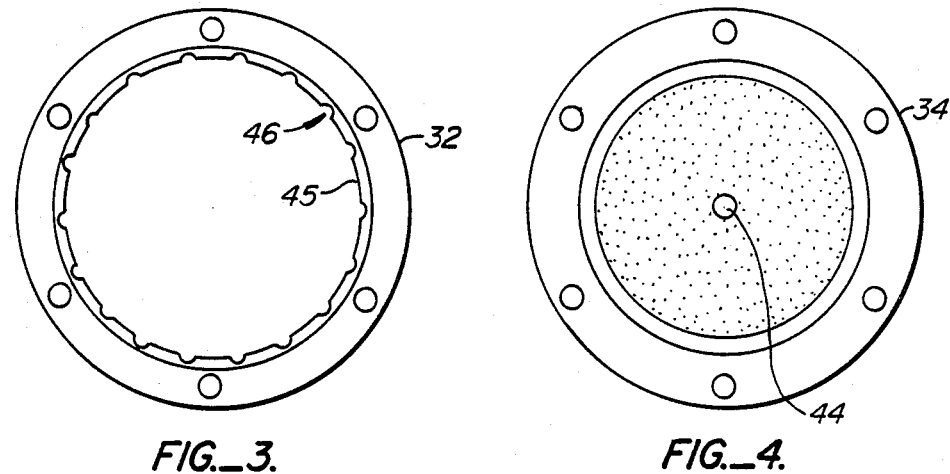
FIG._3.  FIG._4.

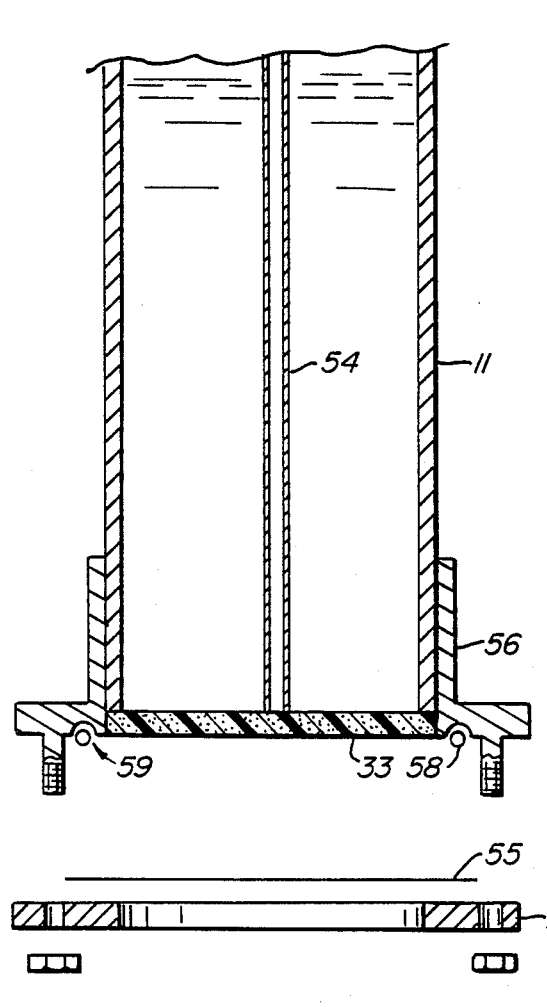

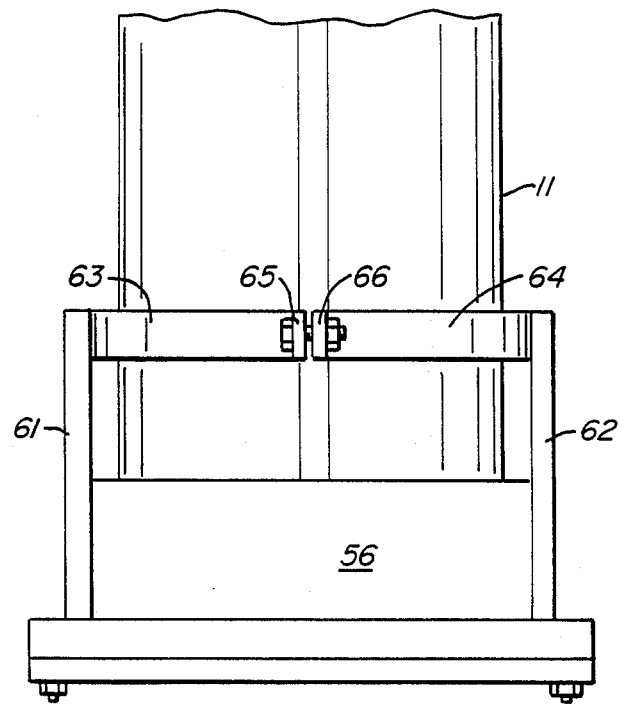
FIG._6a.
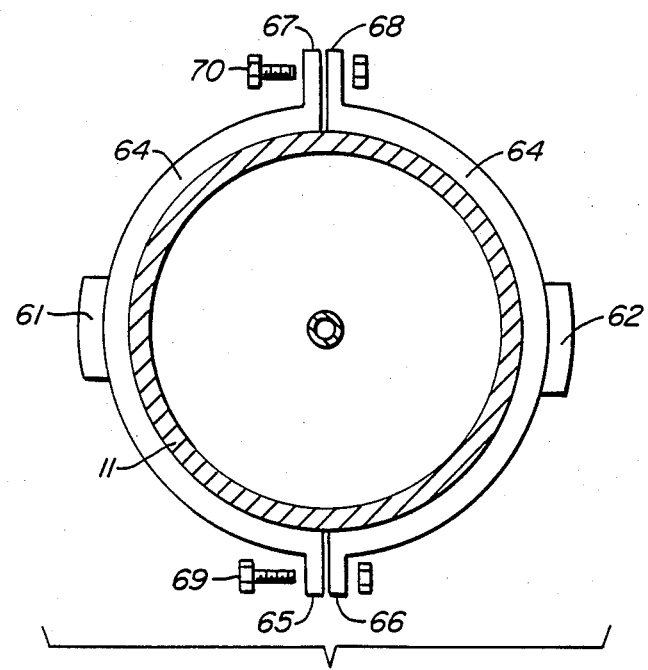
FIG._6b.

APPARATUS FOR PREPARATIVE GEL ELECTROPHORESIS

This invention relates to electrophoretic systems, and in particular to preparative gel electrophoresis.

BACKGROUND AND SUMMARY OF THE INVENTION

As a preparative separation technique, electrophoresis offers the substantial advantage of the ability to separate species which are otherwise very difficult to separate, notably macromolecules and biochemical species in particular. Preparative separations involve the consolidation of solute zones emerging from the column and the transport of these zones to a fraction collector arrangement without permitting them to recombine.

The need to remove the eluting solute zones without disturbing the separation gel or the electrical potential imposed across it has led to some rather complicated and awkward apparatus constructions. Difficulties encountered with these constructions include irregularities in the fluid flow such as dead volumes and eddies which disturb the zones during transport, inadequate support of the separation gel, and complicated procedures for assembly and disassembly.

The present invention overcomes these difficulties by providing apparatus in the form of a collar and associated parts for securement to one open end of a tubular electrophoresis column (hereinafter "the Column"), and designed such that once secured in this manner, it can be immersed in a buffer solution (i.e., the lower buffer solution for a vertical column) to draw small amounts of the buffer solution across the bottom of the Column toward a centrally located point, from which these small amounts of buffer solution, containing eluting solutes, are removed to a fraction collector.

The collar is adapted to secure a porous plate and a dialysis membrane to the open end of the Column, the porous plate defining a space to receive the eluting solutes, and the dialysis membrane isolating the eluting solutes from the lower buffer solution while permitting electrical contact between the gel and the lower buffer solution. The lower buffer solution is drawn into the region of the porous plate through channels in the inside wall of the collar, and the withdrawal port is arranged to draw lower buffer solution from the periphery of the porous plate to a central point, thereby consolidating and collecting each individual solute zone prior to withdrawing it from the gel region.

Among the various preferred embodiments are those in which the collar is adapted to attach to the Column by a clamp and the channels are furrows along the interior wall of the collar, aligned parallel to the collar axis and regularly spaced. The invention extends to systems where the consolidated solutes are drawn down from the Column, in the same direction as the movement of the zones through the Column, as well as those in which the consolidated zones are drawn upward or back through the Column along the Column axis.

Further advantages, embodiments and objects of the invention will be apparent from the following description.

BRIEF DESCRIPTION OF THE DRAWINGS

FIG. 1 is a depiction of one example of an apparatus in accordance with the present invention, shown together with other parts of a full electrophoretic separation system, in a side elevation view in cutaway.

FIG. 2 depicts the collar, porous plate, dialysis membrane and adjoining parts of the example shown in FIG. 1, in exploded form in side elevation.

FIG. 3 is a top view of the collar shown in FIG. 2.

FIG. 4 is a top view of the support plate of FIG. 2.

FIG. 5 depicts an alternative embodiment to the one shown in FIG. 1 with a modified arrangement of the withdrawal tube, the parts shown in side elevation, in cutaway, and in partially exploded form.

FIGS. 6a and 6b depict side elevation and top cutaway views, respectively, of the assembled parts of an illustrative embodiment of the present invention, including a clamp structure for securing the parts to the Column.

DETAILED DESCRIPTION OF THE INVENTION AND PREFERRED EMBODIMENTS

The electrophoretic system shown in FIG. 1 includes a tubular gel enclosure 11, an upper buffer chamber 12 and a lower buffer chamber 13. The lower buffer chamber 13 rests on a support surface (not shown) such as a laboratory bench top. The gel enclosure 11 is held above the lower buffer chamber 13 by any conventional means such as a ring stand clamp (not shown) clamped around the gel enclosure 11 above the level of the lower buffer chamber 13. The upper buffer chamber 12 in this embodiment is constructed to be supported by the gel enclosure 11, resting on top of its upper rim.

The gel shown in this drawing is in two sections, an upper and lower section 14, 15, the two sections differing in gel density, as frequently used in preparative separations. The upper buffer chamber 12 has an opening 16, permitting fluid contact and hence electrical contact between the upper buffer solution 17 and the upper gel section 14. To prevent leakage of the upper buffer solution 17 around the outside of the gel enclosure 1), a gasket 18 such as a rubber O-ring is positioned between the gel enclosure 11 and a sleeve 19 protruding downward from the upper buffer chamber 12 around the opening 16.

The electric potential between the upper buffer solution 17 and the lower buffer solution 23 (which is in electrical contact with the lower end of the lower gel section 15 through the collar 32 at the base thereof, as explained below) is established by electrodes 24, 25 connected to negative and positive terminals 26, 27 respectively joined by a power source 28.

The elements which form the central part of the present invention are shown in FIG. 1 at the lower end of the gel enclosure 11. These elements include the collar 32 sized to fit over the end of the gel enclosure 11, a porous plate 33, which may be fritted glass, porous plastic or the like, a support plate 34, and a dialysis membrane (not visible in this drawing) between the porous plate 33 and the support plate 34. An open passage 35 through the center of the support plate 34 leads to transfer tubing 36 through which liquid is drawn by a pump 37 which in turn directs the fluids to a fraction collector (not shown). All elements, including the power source 28, electrodes 24, 25, porous plate 33, dialysis membrane, transfer tubing 36 and pump 37 are conventional equipment such as those commonly used in electrophoretic separations.

FIG. 2 shows the collar 32, porous plate 33, dialysis membrane 40 and support plate 34 in an exploded view.

All parts are circular in this embodiment. The outer edge 41 of the dialysis membrane 40 is bent over the edge of a central raised portion of the support plate 34, and held in place by a retaining ring 42, which may be a common rubber O-ring or other similar type of element. Although not visible in the drawing, it should further be noted that the dialysis membrane 40 has an opening in the center to permit passage of the solutes eluting from the Column. Inserted in the open passage 35 is a hollow screw 43 which passes through the opening in the center of the dialysis membrane 40 and a hole 44 in the support plate 34 (visible in FIG. 4), and is secured in place by a nut 38. Thus, through the dialysis membrane 40 and the support plate 34, the hollow screw 43 offers a small tubular passage for the solutes from the gel 15. The end of the screw extends a sufficient length to permit the attachment of flexible tubing.

The hollow screw 43 in this embodiment serves two functions. The first is to provide a passage between the lower gel section 15 and the exterior of the gel enclosure 11. The second is to seal the opening in the center of the membrane 40, thereby preventing the eluting solutes from leaking into the lower buffer solution 23. The hole in the center of the membrane 40 should be made as small as possible while of sufficient diameter to permit insertion therein of the body of the hollow screw 43. Once the hollow screw 43 is inserted and fixed in placed by the nut 38, the lower or sloping edge of the screwhead and the slope-shaped opening of the passage 35 will form a tight seal surrounding the opening in the center of the membrane 40, thereby preventing leakage into the lower buffer solution 23.

In assembling the, collar 32, porous plate 33, dialysis membrane 40 and support plate 34 prior to securing these parts to the Column, a leak check may be made as follows. The hole in the hollow screw 43 is first plugged with a small rubber stopper. The collar 32 is then filled with water and placed on tissue paper, where it is permitted to stand, the tissue paper rendering visible any leakage around the hollow screw 43. Leakages thus detected may be corrected by further tightening of the nut 38, or if necessary, by replacing the membrane 40 with a membrane having a smaller center hole.

A top view of the collar 32 appears in FIG. 3. The collar 32 forms a cylinder whose inner wall 45 fits over the gel enclosure 11. Along the inner wall 45 of the collar 32 are a series of furrows 46 which extend from the upper rim 47 of the collar 32 to the lower face 48 of the bottom flange 49 (see FIG. 2). When the collar 32 and the gel enclosure 11 are joined, these furrows 46 form open channels for passage of the lower buffer solution 23 in which this end of the apparatus is submerged. The channels are closed off at the bottom by the support plate 34, but are open to the edges of the porous plate 33, thereby providing feed points spaced around the periphery of the porous plate 33 for entry of the lower buffer solution 17. As the pump 37 (FIG. 1) draws liquid through the hollow screw 43, it in turn draws the lower buffer solution 17 from the lower buffer chamber 13 into the furrows 46 downward to the porous plate 33, then laterally through the porous plate 33 toward the center and finally out through the small tubular passage of the hollow screw 43, which is open at the top to permit entry of the liquid. The arrangement of the furrows 46 and the central location of the open passage 35 causes a lateral sweep of the entire cross section of the bottom end of the gel 15, consolidating the emerging solutes into a narrow stream. The number of furrows or channels is not critical. The number needed will generally depend on the column diameter. In most cases, 6 or more, preferably 12 or more, will be appropriate. In the embodiment shown in FIG. 3, 18 furrows are included.

The collar 32 may be secured to the gel enclosure 11 in any of a variety of ways. In some cases, a friction fit will suffice. In others, particularly where a short gel is used, a friction fit will be insufficient and a clamp will be more appropriate. An example of such a clamp is shown in FIGS. 6a and 6b, discussed in detail below. Selection of the optimum securing means for any particular collar or gel enclosure will be readily apparent to those skilled in the art.

The support plate 34 in the embodiment shown in FIG. 4 is composed of a solid plastic ring and in the middle, a porous plate of somewhat greater thickness than the porous plate 33 in which the solutes eluting from the gel 15 are collected. While other types of support plates may be used, the support plate 34 with a thick porous plate in the middle provides certain advantages, including uniform support over the entire cross section of the apparatus with full and continuous contact between the gel 15 and the lower buffer solution 17. Such support permits the use of a very thin porous plate 33 above the dialysis membrane 40, minimizing the dead volume therein.

A second example of an apparatus within the scope of the invention is depicted in FIG. 5. Here a gel enclosure 11 is shown identical to that shown in FIG. 1. In this case, however, the system is configured to draw the eluting solutes upward through the Column in a withdrawal tube 54 embedded in the gel, and positioned at approximately the center or axis of the gel enclosure 11. This type of arrangement is useful in polyacrylamide gels, whereas the arrangement shown in FIGS. 1 and 2 is useful in both polyacrylamide and agarose gels. A porous plate 33 identical to that shown in FIGS. 1 and 2 is included. The dialysis membrane 55, however, differs from that of FIGS. 1 and 2 in that it contains no central opening since the solutes are not required to pass through it. The design of the collar 56 and support plate 57 are also slightly different from their counterparts in FIG. 2. The support plate 57 is flat, with no central raised portion, and the O-ring 58 rests in a groove 59. The hollow screw 34 is eliminated entirely.

The withdrawal tube 54 is of glass or any other inert solid material, preferably transparent, like the gel enclosure 11. The withdrawal tube 54 is embedded in and held in place by the gel. This is accomplished by conventional procedures, most conveniently by holding the tube in place by external mechanical means while the gel solution is poured into the gel enclosure 11 on a casting stand with the open end at the base sealed off by either a membrane or a gasket. A smooth-surfaced rubber sheet, for example, can seal both the gel enclosure 11 and the withdrawal tube 54.

Once the gel solidifies, the membrane or gasket is removed, and the withdrawal tube 54 is secured in place by the gel. During casting, care is taken to make sure that the lower rims of both the gel enclosure 11 and the withdrawal tube 54 are coplanar, and that the interior of the tube remains open. A tube will be selected of sufficient length to extend above the top surface of the gel. Once the gel is fully formed, transfer tubing similar to that shown in FIG. 1 (the tubing 36) is attached to the emerging tip (not shown) of the withdrawal tube 54. The transfer tubing then passes through the upper buffer solution 17 and out of the upper buffer chamber 12 where it feeds the pump 37. The components shown in these figures, and likewise suitable for use in other embodiments of the invention, may be made from conventional materials. The gel enclosure 11, for example, will generally be made of glass or other materials commonly used for similar purposes. Typical dimensions are approximately 1.5-2 inches outer diameter, ⅛ inch thickness and 4-6 inches in length. The collar may be 1-2 inches in length, and will typically although not necessarily be made of plastic. The voltage imposed across the electrodes will typically range from about 10 to about 20 volts per centimeter length. The withdrawal tube 54 shown in FIG. 5 may be glass tubing of which the smaller the diameter, the better. A typical tube may be of approximately 2 mm outer diameter.

FIGS. 6a and 6b show a clamp structure incorporated into a collar 56 for securement of the collar 56 to the gel enclosure 11. The clamp structure consists of two legs 61, 62 fused to the outer surface of the collar 56 at opposite sides, each leg extending upward above the collar 56. Each leg terminates at its upper end in an arc-shaped brace 63, 64, conforming to the curvature of the gel enclosure 11. Each brace terminates in a flange 65, 66, 67, and 68, through which a screw 69, 70 is passed, tightening the braces against the gel enclosure 11.

The foregoing is offered primarily for purposes of illustration. It will be readily apparent to those skilled in the art that variations may be made in the various elements of structure and operation described herein while still falling within the scope of the invention.

What is claimed is:

1. Apparatus for drawing solutes eluting from an open-ended tubular electrophoresis column having a given cross section into transfer tubing, said apparatus comprising
    a porous plate and a dialysis membrane, both sized to span said cross section, said dialysis membrane being impermeable to said solutes;
    a collar adapted to receive said open end and to secure said porous plate and said dialysis membrane thereto;
    a plurality of channels in said collar communicating the exterior of said collar with a plurality of loci along the interior wall thereof, said loci positioned to reside along the periphery of said open end of said tubular electrophoresis column when said collar is joined thereto; and
    means for drawing fluid from said porous plate at a withdrawal site within the periphery thereof.

2. Apparatus in accordance with claim 1 in which said loci are positioned at substantially regular intervals around said periphery.

3. Apparatus in accordance with claim 1 further comprising means for clamping said collar to said open-ended tubular electrophoresis column.

4. Apparatus in accordance with claim 1 in which said channels are furrows along the interior wall of said collar.

5. Apparatus in accordance with claim 4 in which said open-ended tubular electrophoresis column has an axis and said furrows are parallel to said axis.

6. Apparatus in accordance with claim 4 in which said furrows are spaced at substantially regular intervals along said interior wall.

7. Apparatus in accordance with claim 4 in which said furrows are at least six in number.

8. Apparatus in accordance with claim 4 in which said furrows are at least twelve in number.

9. Apparatus in accordance with claim 1 in which said withdrawal site is approximately at the center of said porous plate.

10. Apparatus in accordance with claim 1 in which said fluid drawing means draws fluid in a direction parallel to the axis of said open-ended tubular electrophoresis column.

11. Apparatus in accordance with claim 10 in which said direction is away from the interior of said open-ended tubular electrophoresis column.

12. Apparatus in accordance with claims 1 or 10 in which said dialysis membrane has an opening to permit passage of said solutes therethrough and said direction is away from the interior of said open-ended tubular electrophoresis column through said opening.

13. Apparatus in accordance with claim 10 in which said fluid drawing means draws fluid through the interior of said open-ended tubular electrophoresis column.

14. Apparatus for preparative electrophoresis, comprising:
    a gel enclosure open at opposite ends;
    upper and lower buffer chambers and means for imposing an electric potential therebetween, said upper buffer chamber adapted to contain an upper buffer solution and to place said upper buffer solution in fluid contact with a first open end of said gel enclosure, and said lower buffer chamber sized to contain a lower buffer solution and to permit immersion of a second open end of said gel enclosure therein;
    a porous plate and a dialysis membrane, both sized to span said second open end, said dialysis membrane being impermeable to said solutes;
    a collar adapted to receive said second open end and to secure said porous plate and said dialysis membrane thereto;
    a plurality of channels in said collar communicating the exterior of said collar with a plurality of loci along the interior wall thereof, said loci position to reside along the periphery of said second open end of said tubular electrophoresis column when said collar is joined thereto; and
    means for drawing fluid from the interior of said collar at a withdrawal site within the periphery of said porous plate to a location outside said lower buffer chamber.

15. Apparatus in accordance with claim 14 in which said channels are furrows along the interior wall of said collar.

16. Apparatus in accordance with claim 15 in which said furrows are spaced at substantially regular intervals along said interior wall.

17. Apparatus in accordance with claim 14 in which said collar is shaped to receive said second open end of said gel enclosure in a friction fit.

18. Apparatus in accordance with claim 14 in which said withdrawal site is approximately at the center of said porous plate.

19. Apparatus in accordance with claim 14 in which said gel enclosure has a central axis and said fluid drawing means draws fluid in a direction parallel to said central axis.

20. Apparatus in accordance in claim 19 in which said direction is away from the interior of said gel enclosure when said collar is joined thereto.

21. Apparatus in accordance with claim 19 in which said dialysis membrane has an opening to permit passage of said solutes therethrough and said direction is away from the interior of said gel enclosure through said opening.

22. Apparatus in accordance with claim 19 in which said fluid drawing means draws fluid through the interior of said gel enclosure.

* * * * *